US006673357B2

(12) United States Patent
Attard et al.

(10) Patent No.: US 6,673,357 B2
(45) Date of Patent: Jan. 6, 2004

(54) ALKALOID GLYCOSIDE FOR USE AS A MEDICAMENT

(75) Inventors: George Simon Attard, Southhampton (GB); William John Woodroofe Morrow, London (GB); Palasingam Rajananthanan, London (GB)

(73) Assignees: University of Southampton, Hampshire (GB); Queen Mary and Westfield College, London (GB)

( * ) Notice: Subject to any disclaimer, the term of this patent is extended or adjusted under 35 U.S.C. 154(b) by 0 days.

(21) Appl. No.: 09/242,442

(22) PCT Filed: Aug. 27, 1997

(86) PCT No.: PCT/GB97/02312

§ 371 (c)(1),
(2), (4) Date: Aug. 27, 1999

(87) PCT Pub. No.: WO98/08544

PCT Pub. Date: Mar. 5, 1998

(65) Prior Publication Data

US 2002/0155118 A1 Oct. 24, 2002

(30) Foreign Application Priority Data

Aug. 30, 1996 (GB) .............................. 9618119

(51) Int. Cl.⁷ .................. A61K 45/00; A61K 47/44
(52) U.S. Cl. ................ 424/283.1; 424/279.1; 424/185.1; 514/24; 514/25; 536/4.1
(58) Field of Search ............ 424/279.1, 185.1, 424/283.1; 536/4.1; 514/24, 25

(56) References Cited

U.S. PATENT DOCUMENTS 5,980,899 A 11/1999 Berzofsky et al.

FOREIGN PATENT DOCUMENTS

| EP | 109942 | 10/1983 |
| EP | 231039 | 1/1987 |
| FR | 5211 | * of 1967 |
| WO | 9110743 | 7/1991 |

OTHER PUBLICATIONS

Roddick, TG. Adv. Exp. Med. Biol. Mar. 1996 404: 277–295.*

Fluka Catalog—Tomatine, 1993.*

Filderman et al. Br. J. Pharm. 37: 748–755.*

XP 002045846; WPI Derwent; AN 73–40638U; "Anti-allergy Comps—Based on Solanine Hydrogen Chloride". Abstract only.

Chemical Abstracts, vol. 88, No. 1, Jan. 2, 1978, Abstract No. 424h; "Effect of Solanine Hydrochloride on Sensitization of Guinea Pigs Under Experimental Conditions". Abstract only.

R. Bomford et al; "Adjuvanticity and ISCOM Formation by Structurally Diverse Saponins", Vaccine; vol. 10, Issue 9, 1992, pp. 572–577.

PCT/GB97/02312; International Search Report mailed Dec. 3, 1997.

* cited by examiner

*Primary Examiner*—Gerald R Ewoldt
(74) *Attorney, Agent, or Firm*—Renner, Otto, Boisselle & Sklar, LLP

(57) ABSTRACT

The invention concerns an alkaloid glycoside for use in medicine. In a preferred aspect, the alkaloid glycoside is used for the stimulation of a class I-restricted immune response and/or a class II-restricted immune response. In a preferred aspect, the alkaloid glycoside is tomatine.

5 Claims, No Drawings

ALKALOID GLYCOSIDE FOR USE AS A MEDICAMENT

The present invention relates to a compound. More especially, the present invention relates to an adjuvant for use in a vaccine. In a more particular embodiment, the present invention relates to a glycoside adjuvant.

In the majority of vaccines used to date antibodies are raised against proteins that are present on the surfaces of disease-causing (pathogenic) organisms (e.g. viruses, bacteria). Vaccine formulations typically contain inactivated or killed pathogens. In many situations it is desirable to elicit an antibody response against a particular set of proteins, peptides or carbohydrates that are present in the pathogen. This leads to a well-defined response which can be targeted against proteins that are highly conserved between different strains of the pathogen, thereby achieving a broader-based immunity.

Furthermore, the ability to stimulate both class I- and class II-restricted immune responses is deemed to be important because it leads to a more comprehensive level of immunity than is currently achieved with existing vaccines.

Briefly, class II-restricted responses involve the production of antibodies that are specific to the proteins or peptides used in the vaccine—this is often referred to as the humoral immune response.

Class I-restricted immune responses are cell-mediated responses that are responsible for detecting and dealing with viral infections. In contrast to the class II-restricted responses, class I responses involve the activation of CD8+ cytotoxic T lymphocytes (CTLs). These CTLs are activated by oligomeric peptides that are derived from non-self proteins. These peptides are presented at the surface of cells in conjunction with the products of the major histocompatibility complex I (MHC-1). Activated CTLs are able to recognise and destroy virus-infected cells that have non-self oligopeptides on their surfaces.

The use of adjuvants in vaccine formulations leads to enhanced immune responses, particularly against soluble proteins and peptides which are only weakly immunogenic.

Several adjuvants have been described in the literature (e.g. complete or incomplete Freund's adjuvant) but most are only of experimental interest because of their severe inflammatory side-effects. So far, saponin-based adjuvants are believed by some to be amongst the most promising because of their activity and their relatively low toxicity and inflammatory side-effects.

By way of example, EP-A-0231039 discloses the use of a saponin glycoside as an adjuvant for vaccines. These particular adjuvants, which are in the form of nanoparticles, are characterised by their unique architectures and are often referred to as immunostimulatory complexes (ISCOMS). These are produced by mixing a saponin glycoside and cholesterol in aqueous solutions, often in the presence of a lipid and detergent, followed by one or more purification steps. The saponin is present in at least its critical micellar concentration (CMC). The ability of ISCOMS to elicit high antibody titres against a wide range of antigenic proteins and peptides has been demonstrated as has their ability to induce CTL activity (i.e. the ISCOM nanoparticles can stimulate both class I- and class II-restricted immune responses).

However, there is still a continuing need to develop adjuvants for vaccines, in particular adjuvants that can stimulate class I-restricted and/or class II-restricted immune responses to naturally occurring or synthetic proteins and oligopeptides.

According to a first aspect of the present invention there is provided an alkaloid glycoside for use in medicine.

According to a second aspect of the present invention there is provided an alkaloid glycoside for the stimulation of a class I-restricted immune response and/or a class II-restricted immune response.

According to a third aspect of the present invention there is provided an alkaloid glycoside for use as a vaccine adjuvant.

According to a fourth aspect of the present invention there is provided the use of an alkaloid glycoside in the manufacture of a medicament for use as a vaccine.

According to a fifth aspect of the present invention there is provided the use of an alkaloid glycoside as an adjuvant in the manufacture of a medicament for use as a vaccine.

According to a sixth aspect of the present invention there is provided the use of an alkaloid glycoside in the manufacture of a medicament to stimulate a class I-restricted immune response and/or a class II-restricted immune response.

According to a seventh aspect of the present invention there is provided a process of preparing a composition comprising admixing an agent capable of inducing an immune response with an alkaloid glycoside, wherein the agent is in an amount to cause an induction of an immune response and wherein the alkaloid glycoside is in an amount for use as an adjuvant.

According to an eighth aspect of the present invention there is provided a process of preparing a composition comprising admixing an agent capable of inducing an immune response with an alkaloid glycoside, wherein the agent is in an amount to cause an induction of an immune response and wherein the alkaloid glycoside is in an amount to cause stimulation of a class I-restricted immune response and/or a class II-restricted immune response.

According to a ninth aspect of the present invention there is provided a method of treatment, the method comprising administering to a subject a composition wherein the composition comprises an agent capable of inducing an immune response within the subject and wherein the composition also comprises an alkaloid glycoside, wherein the agent is in an amount to cause an induction of an immune response and wherein the alkaloid glycoside is in an amount for use as an adjuvant.

According to a tenth aspect of the present invention there is provided a method of treatment, the method comprising administering to a subject an alkaloid glycoside, wherein the alkaloid glycoside is in an amount to cause stimulation of a class I-restricted immune response and/or a class II-restricted immune response.

According to an eleventh aspect of the present invention there is provided a method of treatment, the method comprising administering to a subject in need of treatment a composition wherein the composition comprises an agent capable of inducing an immune response within the subject and wherein the composition also comprises an alkaloid glycoside, wherein the agent is in an amount to cause an induction an immune response and wherein the alkaloid glycoside is in an amount to cause stimulation of a class I-restricted immune response and/or a class II-restricted immune response.

According to a twelfth aspect of the present invention there is provided the combination of an alkaloid glycoside and an agent capable of inducing an immune response.

According to a thirteenth aspect of the present invention there is provided the combination of two or more compositions for sequential or consecutive administration to a subject, wherein at least one composition comprises an alkaloid glycoside and at least one other composition comprises an agent capable of inducing an immune response.

Thus, the present invention is based on the surprising finding that it is possible to use an alkaloid glycoside for a medical usuage, in particular for the stimulation of a class I-restricted immune response and/or a class II-restricted immune response. This finding is highly surprising as R. Bomford, M. Stapleton, J. E. Beesley, E. A Jessup, K. R. Price, G. R. Fenwick (in "Adjuvanticity and ISCOM formation by structurally divests saponins"; *Vaccine*, vol.10, (1992), 572–577.) state that glycoalkaloids (i.e. alkaloid glycosides) lack adjuvant activity.

The term "subject" includes any one or more different types of animal, including humans. Preferably, the term means a human.

The term "glycoside" as used herein means a derivative of a sugar (which may be a simple sugar or a complex sugar) in which the hydroxyl group attached to carbon 1 of the sugar is substituted by an alcoholic, or other, aglycone group.

In a preferred embodiment, the term "glycoside" as used herein means a chemical entity/substance comprising a steroid, triterpene or other polycyclic aliphatic structure and one or more carbohydrates.

The term "alkaloid glycoside" as used herein means a glycoside capable of combining with acids to form salts.

In a preferred embodiment, the term "alkaloid glycoside" as used herein means a glycoside where the aglycone group is a steroid, triterpene or other polycylic aliphatic structure which contains at least one nitrogen heterocycle (i.e. a heterocyclic group comprising at least N).

Preferably, the nitrogen heterocycle is a derivative of pyrrolidine, piperidine, imidazoline, piperazine, morpholine, pyridine, quinoline, isoquinoline, or pyrimidine.

Preferably the alkaloid glycoside is substantially (virtually) water insoluble.

Preferably, the term "substantially (virtually) water insoluble" means having a solubility of less than 300 mg per 1000 cc $H_2O$.

Examples of suitable alkaloid glycosides may include tomatine, chaconine commersonine, demissine, solanine and solasonine.

For the present invention the alkaloid glycoside may be a specific alkaloid glycoside or it may be a mixture of alkaloid glycosides.

Preferably, the alkaloid glycoside is at least tomatine (viz. (3β, 5α, 22β, 25S)-Spirosolan-3-yl O-β-D-glucopyranosyl-(1-2)-O-[β-D-xlopyranosyl-(1-3)]-O-β-D-glucopyranosyl-(1-4)-β-D-galactopyranoside).

Preferably, the alkaloid glycoside is tomatine.

In each of the aspects of the present invention the alkaloid glycoside may be used in combination with one or more other adjuvants, such as saponin glycoside.

In each of the aspects of the present invention the alkaloid glycoside may be used in combination with one or more pharmaceutically acceptable carrier(s) and/or diluent(s) and/or excipient(s).

In each of the aspects of the present invention the alkaloid glycoside may be used in combination with one or more other active agent(s).

The composition of the present invention may be used for prophylactic treatment or for curative treatment.

Preferably, the composition of the present invention may be used for prophylactic treatment.

Preferably, the composition is a vaccine composition.

Preferably, the composition of the present invention is translucent.

Preferably the method of treatment is a method of vaccination or immunisation.

In the method of treatment, the alkaloid glycoside may be administered at—or delivered to—a different site on or in a subject than some or all of the agent that is capable of inducing an immune response.

Preferably, the immune response is at least partial vaccination or immunisation.

More preferably, the immune response is substantial vaccination or immunisation.

In a preferred aspect, the agent capable of inducing an immune response is a protein or oligopeptide.

Typically, the protein or oligopeptide is isolatable from a virus, a bacterium, a parasite, or an animal cell.

In a more preferred aspect, the agent capable of inducing an immune response is a naturally occurring protein or oligopeptide or a synthetic protein or oligopeptide.

Here the term "synthetic" includes proteins or oligopeptides made by recombinant DNA techniques and/or proteins or oligopeptides made by synthetic chemical techniques.

Preferably, the protein or oligopeptide is equivalent to a T cell epitope.

For some applications, the protein or oligopeptide may be water soluble.

Preferably, the term "water soluble" means " means having a solubility of at least 300 mg per 1000 cc $H_2O$.

For some applications, the protein or oligopeptide may be more water soluble than the alkaloid glycoside.

More preferably the protein or oligopeptide is weakly immunogenic. The term "weakly immunogenic" means that when administered in the absence of adjuvants, the agent induces less than a tenfold increase in antibody titres or less than 45% cell lysis in an assay of CTL activity.

For some applications, preferably the protein or oligopeptide is substantially purified prior to admixture with the alkaloid glycoside.

With the present invention, the alkaloid glycoside may be used in combination with one or more agents capable of inducing an immune response.

For some applications, preferably the alkaloid glycoside is used in combination with one specific type of agent capable of inducing an immune response.

Preferably, the alkaloid glycoside of the present invention is used to stimulate both class I-restricted and class II-restricted immune responses.

More preferably, the alkaloid glycoside of the present invention is used to stimulate both class I-restricted and class II-restricted immune responses to naturally occurring or synthetic proteins and oligopeptides.

In the combination aspect of the present invention, the alkaloid glycoside need not necessarily be admixed with the agent capable of inducing an immune response. Preferably, however, the alkaloid glycoside is admixed with the agent capable of inducing an immune response.

In a preferred aspect, the alkaloid glycoside may be admixed with an agent that is capable of suppressing the haemolytic activity of the alkaloid glycoside.

A preferred agent that is capable of suppressing the haemolytic activity of the alkaloid glycoside is a sterol.

Preferred sterols that are capable of suppressing the haemolytic activity of the alkaloid glycoside are sterols of animal or plant origin and may include any one or more of cholesterol, stigmasterol, lumisterol.

A highly preferred agent that is capable of suppressing the haemolytic activity of the alkaloid glycoside is cholesterol.

In a preferred aspect, the alkaloid glycoside may be admixed with a solubiliser for the alkaloid glycoside—particularly if the alkaloid glycoside is substantially insoluble in water.

In a preferred aspect, the solubiliser is a detergent.

Suitable detergents include any one or more of a non-ionic detergent, an ionic detergent, and a zwitterionic detergent.

Preferably, the detergent is at least a non-ionic detergent.

Preferably, the detergent is a non-ionic detergent.

A preferred detergent is β-octylglucopyranoside.

If a detergent is used, then preferably the detergent is removed from the composition that is to be used for the method of treatment. In this regard, the art is replete with techniques to remove detergents. By way of example, the detergent is removed by dialysis, chromatography or gradient centrifugation. Preferably, the detergent is removed by dialysis.

The composition of the present invention may also include other components—such as one or more lipids.

In a more preferred aspect, the composition of the present invention thus comprises tomatine, cholesterol, a non-ionic detergent, and saline. Cholesterol is present to suppress the haemolytic activity of tomatine. Since tomatine is virtually insoluble in water, the non-ionic detergent is employed to solubilise it. The mixture is dialysed against saline to remove the detergent. In this way the adjuvant formulation is obtained as a translucent dispersion.

With the present invention, the alkaloid glycoside may be administered subsequent to, and/or consecutive with, and/or prior to administration of the agent capable of inducing an immune response. Preferably, at least some of the alkaloid glycoside is administered consecutively with at least some of the agent capable of inducing an immune response.

For some applications, preferably at least a substantial proportion of the alkaloid glycoside is administered consecutively with at least a substantial proportion of the agent capable of inducing an immune response.

With the present invention the some or all of the alkaloid glycoside may be administered in the same composition as some or all of the agent capable of inducing an immune response.

Alternatively, the alkaloid glycoside may be administered in a different composition as the agent capable of inducing an immune response.

Preferably, the alkaloid glycoside is administered in the same composition as the agent capable of inducing an immune response The present invention will now be described by way of example only. In the following examples, room temperature was 20° C.

EXAMPLE 1

{Preparation of composition RAM-1*—which comprises an adjuvant according to the present invention and an agent capable of inducing an immune response.}

Part A 25 mg tomatine, 3.1 mg phosphatidylethanolamine and 125 mg β-octylglucopyranoside were added to 4 ml of saline (0.9% sodium chloride solution). The mixture was warmed to 60° C. and shaken vigorously over a two hour period using a vortex mixture until a uniform faintly cloudy dispersion was obtained. The mixture was allowed to cool to room temperature before use.

Part B 6.25 mg cholesterol, 3.1 mg phosphatidylethanolamine and 125.0 mg β-octylglucopyranoside were added to 3 ml of saline (0.9% sodium chloride solution). The mixture was warmed to 50° C. and shaken vigorously using a vortex mixer until a clear solution was obtained. The mixture was allowed to cool to room temperature before use.

Part C 25 mg ovalbumin (OVA) was dissolved in 3 ml of saline (0.9% sodium chloride solution) at room temperature.

Part A was mixed with Part B and shaken vigorously over a period of two hours. To this mixture was added Part C followed by vigorous shaking. The mixture was placed in a thermostatted water bath at 35° C. for 12 hours and shaken regularly during this period. After the mixture was allowed to cool to room temperature it was placed in a dialysis tube (Mr 10000 cut-off) and dialysed against saline for 24 hours to produce the adjuvant formulation RAM-1*.

EXAMPLE 2

{Preparation of composition RAM-1—which comprises an adjuvant according to the present invention (but no agent capable of inducing an immune response).}

Part A 25 mg tomatine, 3.1 mg phosphatidylethanolamine and 125 mg β-octylglucopyranoside were added to 4 ml of saline (0.9% sodium chloride solution). The mixture was warmed to 60° C. and shaken vigorously over a 2 hour period using a vortex mixture until a uniform faintly cloudy dispersion was obtained. The mixture was allowed to cool to room temperature before use.

Part B 6.25 mg cholesterol, 3.1 mg phosphatidylethanolamine and 125.0 mg β-octylglucopyranoside were added to 3 ml of saline (0.9% sodium chloride solution). The mixture was warmed to 50° C. and shaken vigorously using a vortex mixer until a clear solution was obtained. The mixture was allowed to cool to room temperature before use.

Part A was mixed with Part B and shaken vigorously over a period of two hours. To this mixture was added 3 ml of saline (0.9% sodium chloride solution) followed by vigorous shaking. The mixture was placed in a thermostatted water bath at 35° C. for 12 hours and shaken regularly during this period. After the mixture was allowed to cool to room temperature it was placed in a dialysis tube (Mr 10000 cut-off) and dialysed against saline for 24 hours to produce the adjuvant formulation RAM-1.

EXAMPLE 3

{Preparation of composition RAM-2*—which comprises an adjuvant according to the present invention and an agent capable of inducing an immune response.}

Part A 99 mg tomatine, 12.5 mg phosphatidylethanolamine and 495 mg β-octylglucopyranoside were added to 4 ml of saline (0.9% sodium chloride solution). The mixture was warmed to 50° C. and shaken vigorously over a two hour period using a vortex mixer until a uniform faintly cloudy dispersion was obtained. The mixture was allowed to cool to room temperature before use.

Part B 25 mg cholesterol, 12.5 mg phosphatidylethanolamine and 495 mg β-octylglucopyranoside were added to 3 ml of saline (0.9% saline chloride solution). The mixture was warmed to 50° C. and shaken vigorously using a vortex mixer until a clear solution was obtained. The mixture was allowed to cool to room temperature before use.

Part C 10 mg ovalbumin (OVA) was dissolved in 3 ml of saline (0.9% sodium chloride solution) at room temperature.

Part A was mixed with Part B and shaken vigorously over a period of two hours. To this mixture was added Part C followed by vigorous shaking. The mixture was placed in a thermostatted water bath at 35° C. for 12 hours and shaken vigorously during this period. After the mixture was allowed to cool to room temperature it was placed in a dialysis tube (Mr 3000 cut-off) and dialysed against saline for 24 hours to produce the adjuvant formulation RAM-2*.

EXAMPLE 4

{Preparation of composition RAM-2—which comprises an adjuvant according to the present invention (but no agent capable of inducing an immune response).}

Part A 99 mg tomatine, 12.5 mg phosphatidylethanolamine and 495 mg β-octylglucopyranoside were added to 4 ml of saline (0.9% sodium chloride solution). The mixture was warmed to 50° C. and shaken vigorously over a two hour period using a vortex mixer until a uniform faintly cloudy dispersion was obtained. The mixture was allowed to cool to room temperature before use.

Part B 25 mg cholesterol, 12.5 mg phosphatidylsethanolamine and 494 mg β-octylglucopyranoside were added to 3 ml of saline (0.9% sodium chloride solution). The mixture was warmed to 50° C. and shaken vigorously using a vortex mixer until a clear solution was obtained. The mixture was added to cool to room temperature before use.

Part A was mixed with Part B and shaken vigorously over a period of two hours. To this mixture was added 3 ml of saline (0.9% sodium chloride solution) followed by vigorous stirring. The mixture was placed in a thermostatted water bath at 35° C. for 12 hours and shaken regularly during this period. After the mixture was allowed to cool to room temperature it was placed in a dialysis tube (Mr 3000 cut-off) and dialysed against saline for 24 hours to produce the adjuvant formulation RAM-2.

Antibody Titre Assays

Four sets of experiments were carried out as shown in Table 1. Each group consisted of six mice.

TABLE 1

| Group I | Antigen given subcutaneously (s.c.) at t = 0 (no adjuvants) |
| Group II | RAM-1* or RAM-2* given s.c. at t = 0 |
| Group III | RAM-1 or RAM-2 given s.c. at t = 0 followed by separate injection or antigen at different site 3 hours later |
| Group IV | RAM-1 or RAM-2 given s.c. at t = 0 (no antigen) |

The immunisation/bleeding regime is shown Table 2 below.

TABLE 2

| Immunisation | 1st | 2nd | 3rd | 4th | — | — |
| --- | --- | --- | --- | --- | --- | --- |
| Days | 0 | 7 | 21 | 35 | 56 | 84 |
| Weeks | 0 | 1 | 3 | 5 | 8 | 12 |
| Bleeding (pre) | 1 | 2 | 3 | 4 | 5 | 6 |

The results of the experiments were as follows. Anti-OVA specific antibody titres in the blood serum obtained on day 35 from C57BL/6 mice are shown in Table 3. These titres were measured using standard ELISA procedures and are expressed as logarithm to the base 10 of the highest dilution giving an optical density (OD) reading of >0.1. The background OD was determined by taking the mean of samples from 6 non-immunized mice.

TABLE 3

| | GROUP I | GROUP II | GROUP III | GROUP IV |
| --- | --- | --- | --- | --- |
| $\log_{10}$ antibody titre | 2.7 | 6.0 | 3.3 | 2.0 |

The results showed that all adjuvants lead to high titres of antigen-specific antibodies during the course of the immunisation. Comparison of the data from the Group II and Group III experiments indicate that the adjuvant effect can be achieved by independent administration of antigen and antigen-free adjuvant formulation. None of the Group I or IV experiments showed increases in antigen-specific antibody titres.

Cytotoxicity Assays

Cytotoxic activity mediated by T lymphocytes was measured using the ovalbumin-transfected EL4 (C57BL/6, H-2b thymoma) monoclonal murine cell line as a target. Untransfected EL4 cells were used as negative controls. Spleen cells ($3 \times 10^7$) from normal or immunised mice primed 14 days earlier were incubated with $1.5 \times 10^6$ irradiated (200 Gy) 15–12 cells (gp160 transfectants) or 3T3 cells (which served as controls) for 5 days. Target cells ($1 \times 10^6$) were labelled with 100 $\mu$Ci $^{51}$Cr. Target cells were washed three times in RPMI 1640 medium, diluted to $2 \times 10^5$ cells/ml, and 50$\mu$ ($10^4$) of target cells added to each microtitre well containing antigen or peptide (10 $\mu$M) and preincubated for 30 min. Effector cells were resuspended in complete mdium (CM) to yield a range of effector: target (E:T) ratios. Target cells ($10^4$) were then incubated at different E:T ratios in a total volume of 200 $\mu$l of 10% CM for an additional 4 h. Supernatants (100 $\mu$l) were collected and counted for $^{51}$Cr release. Spontaneous release and maximal release values were determined by incubating target cells in 10% CM alone or 0.1% Triton X-100. Percent Cytotoxicity was calculated using the formula:

$$100 \times (ER-SR)/(MR-SR)$$

where ER is experimental release, SR is spontaneous release and ER is maximal release. The results shown are shown in Table 4 and represent the means of triplicate determinations.

TABLE 4

| | % of Cytotoxic lysis | | |
|---|---|---|---|
| E:T ratio | antigen only | alum + anitgen | RAM-1* |
| 100:1 | 45 | 12 | 60 |
| 50:1 | 30 | 4 | 40 |
| 25:1 | 19 | 3 | 33 |
| 12.5:1 | — | — | 6 |

SUMMARY

In accordance with the present invention, we have found that alkaloid glycosides—such as tomatine—are able to elicit a strong class I- and class II-restricted immune response when administered with soluble proteins.

Other modifications will be apparent to those skilled in the art. For example, solanine or chaconine may be used instead of or in addition to tomatine. By way of further example, any one or more of: Gp120 from human immunodeficiency virus, nucleoprotein from influenza virus, PI outer membrane protein from Neisseria gonorrhoeae, or 055:B5 polysaccharide from *Escherichia coli* may be used instead of or in addition to OVA.

What is claimed is:

1. A medicine comprising one or more alkaloid glycosides and at least one agent which is a protein or oligopeptide, wherein one of the alkaloid glycosides is tomatine, and wherein the agent is capable of inducing an immune response.

2. The medicine of claim 1 wherein the alkaloid glycoside is present in an amount for the stimulation of a class I-restricted immune response and/or a class II-restricted immune response.

3. The medicine according to claim 1, wherein the agent capable of inducing an immune response is weakly immunogenic.

4. The medicine of claim 1 wherein the medicine is a vaccine or vaccine adjuvant.

5. The medicine of claim 1, wherein the medicine stimulates a class I-restricted immune response and/or a class II-restricted immune response.

* * * * *